June 28, 1955 L. M. BARTLETT Plant Pat. 1,402
LIGUSTRUM PLANT
Filed June 29, 1953 2 Sheets-Sheet 1
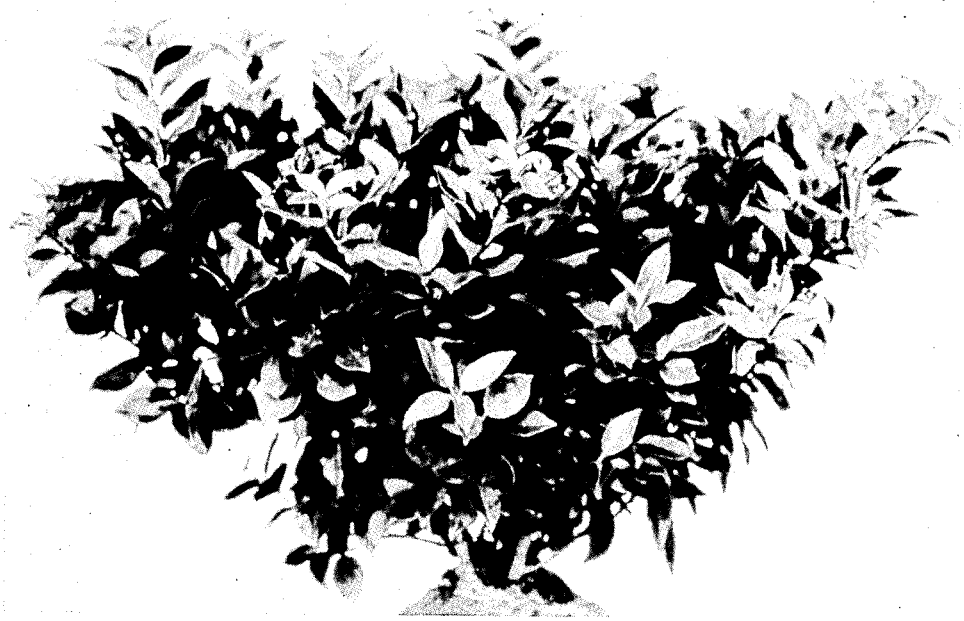
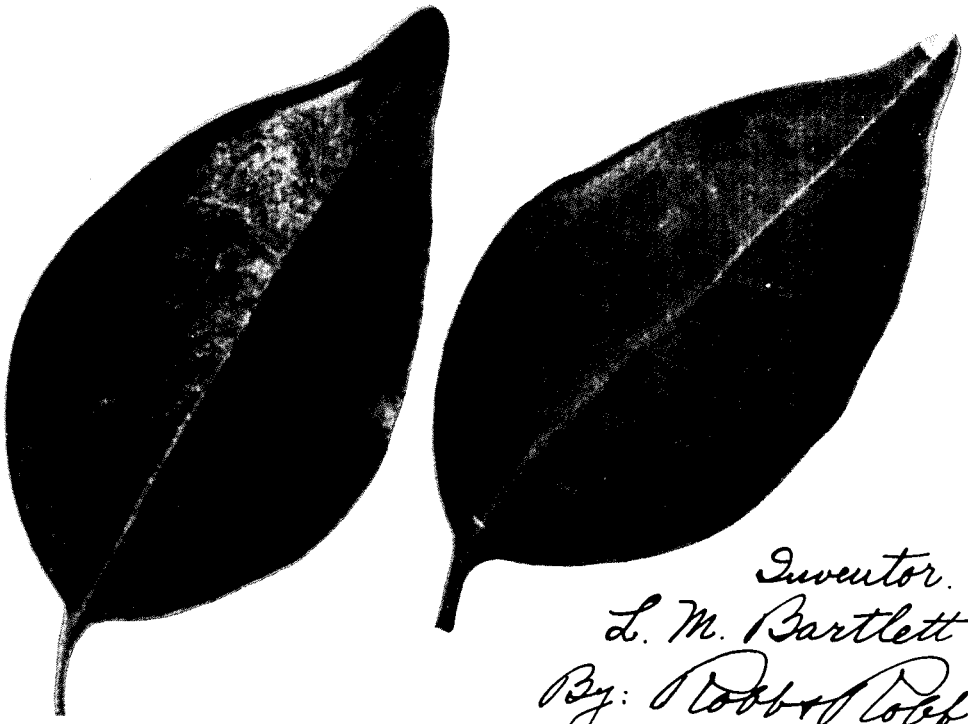
Inventor.
L. M. Bartlett
By: Robb & Robb
Attorneys.

June 28, 1955 L. M. BARTLETT Plant Pat. 1,402
LIGUSTRUM PLANT
Filed June 29, 1953 2 Sheets-Sheet 2
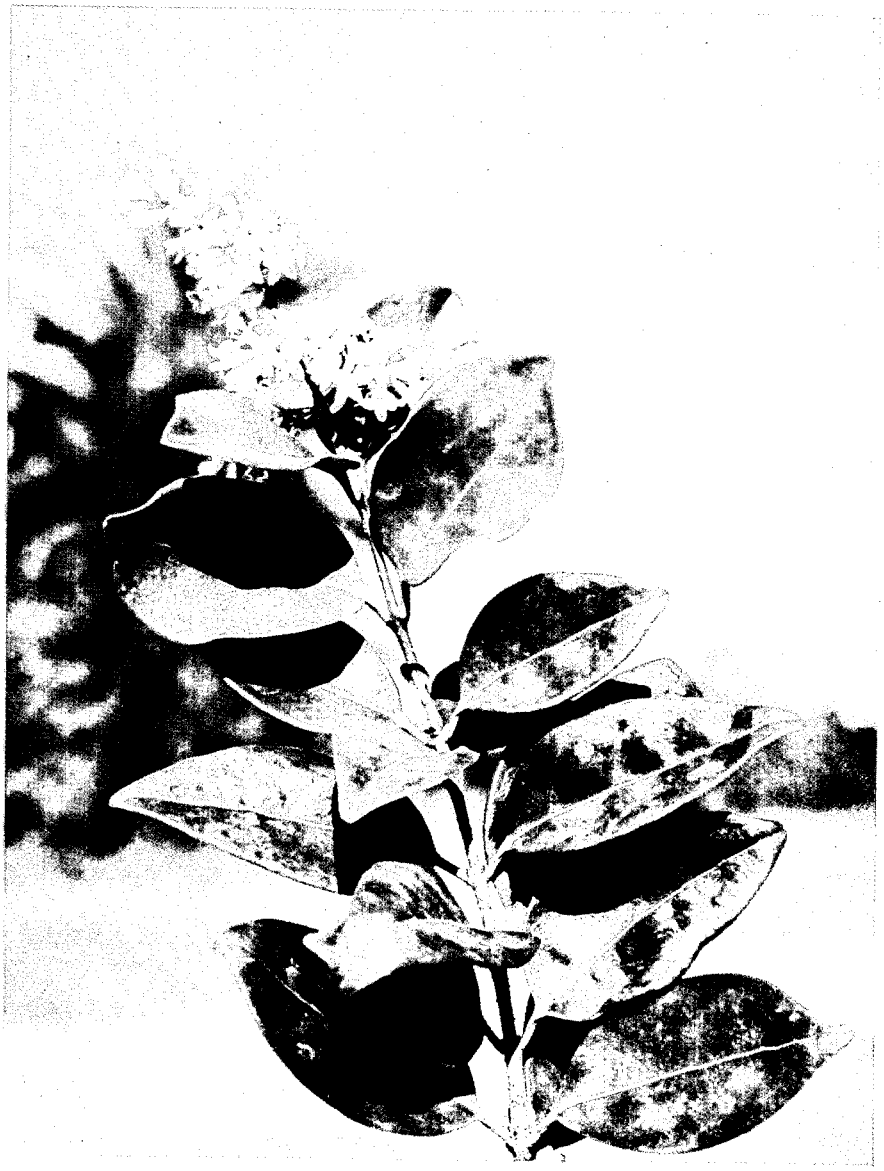
Inventor.
L. M. Bartlett
By: Robb & Robb
Attorneys.

United States Patent Office

Plant Pat. 1,402

Patented June 28, 1955

1,402

LIGUSTRUM PLANT

Larry M. Bartlett, Forest Park, Ga., assignor to Wight Nurseries, Cairo, Ga., a partnership Application June 29, 1953, Serial No. 364,978

1 Claim. (Cl. 47—59)

The present invention or discovery relates to a new and distinct variety of Ligustrum plant which was originated by me by crossing the variety "*Ligustrum japonicum* Thumb." (unpatented) with the variety "*Ligustrum coriaceum* Carr." (unpatented).

As the result of this breeding, I have produced a new variety of Ligustrum plant which is distinguished from its parents, as well as from all other Ligustrum varieties of which I am aware, and which is primarily characterized as to novelty by its dwarf and spreading habits of growth, its short internodes, and by its abundant foliage which almost completely hides the woody stems between nodes.

Evergreen types of Ligustrum, of which "*L. japonicum*" and "*L. coriaceum*" are examples, have value in the horticultural trade largely due to their foliage features, growth habits, and relative growth rates. Their flowers and/or inflorescences are generally not regarded as significant, and prolific fruit development is, more often than not, considered deleterious, since the fruits are rather non-descript from an ornamental standpoint.

The features of novelty of my new variety which is the subject of this application reside in its distinct combination of qualities of foliage, growth habit and growth rate, as compared with those of its parent varieties. It is still further distinguished from either parent by the extreme paucity in the number of fruits developed, although this is not an uncommon attribute of a hybrid.

In order to fully portray the novel features of my new variety, a brief description of the pertinent characteristics of each parent is given in the following, so that the new variety herein may be more readily compared with and contrasted from the parent varieties.

The leaves of "*L. japonicum*" are ordinarily from roundish-ovate to ovate-oblong, with their apieces acute to obtuse, said leaves usually being from 2 inches to 3½ inches long. The leaf blades are only slightly channeled from the margins toward the midribs, and are very definitely not curled. The opposite pairs of leaves are two-ranked on the stems, but the growth response of the petioles to light is such that all of the blades become oriented in an erect fashion along the upper sides of the branches. The lower sides of the branches, therefore, appear rather naked as seen from the side. The nodes are relatively distant, up to 2 inches, or slightly more, apart. Only a few of the axillary buds near the terminus of an annual segment of growth normally develop, and the axillary branches they form tend to spread. These various characteristics contribute to an overall rather open growth habit, with much woody stem visible.

On the other hand, the leaves of "*L. coriaceum*" are from oblong to orbicular, with the apices obtuse-truncate to emarginate, and the blades average about 1-inch in length. The blades are either markedly channeled from the margins toward the midribs, or more often, each half of the blade is curled, and the halves are unequal, so that all the leaves have a decided twisted-curled appearance. They are conspicuously veiny both above and below. The opposite pairs of leaves are two-ranked, as in "*L. japonicum*," but the petioles do not twist in response to light, and are, therefore, oriented around the twig. The internodes are very short, and are rarely over ½ inch in length. The combined effect of the definitely two-ranked pairs of leaves and short internodes is a compact, imbricated leafiness of the individual branches. However, the branches tend to grow rigidly erect, so that the overall growth effect is more or less columnar. In this parent variety, as well as in "*L. japonicum*," only the several axillary buds nearest the terminus of a branch give rise to axillary branches in succeeding seasons. The net result of this, again, is an open growth habit.

My new variety, which was produced from a cross of the two parents described above, has some features of both parents, with one particular growth pattern peculiarly unlike either, and a growth rate falling between them.

The leaf blades of the new variety are more nearly like those of the "*L. japonicum*" parent in outline shape, being roundish-ovate to ovate-oblong, with the apices acute to obtuse. Although like the "*L. japonicum*" parent in general shape, the leaves are intermediate in size in comparison with those of the two parent varieties, most of them being from 1½ inches to 2 inches in length, and they have some of the twisted-curled appearance of the leaves of "*L. coriaceum*." However, the leaf blades of my new variety tend to be twisted or curled only on one side of the midribs, rather than on both sides as in the parent last-mentioned. Also as in the parent "*L. coriaceum*," the petioles of my new variety do not twist in response to light, with the result that the pairs of leaves, which occur in two-ranks, are oriented around the stem. The internodes of the primary branches of the new variety are short, averaging about ½ inch in length. A very distinctive feature of the new variety is the fact that practically all the axillary buds of any previous year's annual segment of growth develop into spreading axillary branches.

The comparative growth rates of my new variety and its parent varieties reveal a marked difference. "*L. japonicum*" grows rather rapidly under normal cultural conditions, and in the latitudes of the Southeastern States, a 10-year old plant would be expected, if unpruned, to reach a height of at least from 15 feet to 20 feet. Known plants of "*L. coriaceum*" grown in the same area under distinctly favorable cultural conditions have attained a height of only 4½ feet to 5 feet in 25 years. The first plants propagated from my new variety, and which are now 12 years old, average about 5 feet in height. On this basis, if comparisons be made between my new variety and some of the other more commonly utilized Ligustrum species, my new variety would be regarded as dwarf or dwarfish, such values being relative in different plant groups.

The flowers and inflorescences of my new variety differ from those of the parents by scarcely perceptible quantative characteristics which do not contribute significantly to its novelty. Their high degree of apparent sterility, although not a visible characteristic in itself, is the most significant thing about them.

The overall appearance or growth habit of the new variety is very markedly distinguishable from that of its respective parents. This innovation is the net result of a new combination of heritable characteristics. It is a compact, bushy-branched shrub, possessing a very large number of axillary branches set close together. The leaves on the numerous branches are of an intermediate size as compared with those of the parents, and being as numerous as those of the "*L. coriaceum*" parent, where they appear imbricated, the result is a much more compact and leafy plant than either parent. Moreover, the individual leaves have some of the twist or curl of the "*L. coriaceum*" parent, even though shaped more like those of the "*L. japonicum*" parent.

Asexual reproduction of the new variety by cuttings at Forest Park, Georgia, shows that the foregoing characteristics and distinctions come true to form and are established and transmitted through succeeding propagations.

In the drawings, one of the drawings shows in black-and-white a typical specimen plant of my new variety, together with enlarged views of typical leaf specimens, the latter views showing respectively the upper and lower surfaces of the leaf, while the other drawing depicts in color a specimen branch section bearing a flower panicle at the terminus thereof.

The following is a detailed description of my new variety, with color terminology in accordance with Maerz & Paul Dictionary of Color, except where general color terms of ordinary signficance are obvious:

Parentage: Seedling—seed parent—"*L. Japonicum.*" Pollen Parent—"*L. Coriaceum.*"

Propagation: Holds its distinguishing characteristics through succeeding propagations by cuttings.

PLANT (Observations made from plants grown at Forest Park, Georgia)

Form: Dwarfish; densely branched; with nearly all axillary buds developing; internodes short, with leaves approximate.

Growth habit: Dwarfish; upright; compact-spreading; relatively slow rate of growth; attains a height of only about 5 feet in 12 years.

Blooming season: Late spring (April, in south Georgia).

Foliage: Leaves opposite; pairs are two-ranked on the twigs; leaf blades also two-ranked, since the petioles do not twist in response to light; internodes about ½ inch in length.

*Size.*—Petioles ¼ inch long; blades from 1 inch to 3 inches long, with the majority from 1½ inches to 2 inches long, and mostly from ¾ inch to 1 inch wide.

*Quantity.*—Very abundant; older leaves tend to remain on the twigs more than one season; short nodes, opposite leaves and extensive branching contributing to an extreme leafiness.

*Color.*—New foliage: upper side—Light Green, Plate 21 L 8; under side—Yellowish Green, Plate 21 L 5. Old foliage: upper side—Dark Green, Plate 23 L 8; under side—Light Green, Plate 21 K 6.

*Shape.*—Roundish-ovate; elliptic to ovate-oblong, with apices acute; somewhat acuminate or obtuse; bases rounded.

*Texture.*—Sub-coriaceous; glabrous on both surfaces; principal veins not apparent from above, and indistinct from below. Upper surface—relatively dark and semi-glossy. Lower surface—pale.

*Edge or margin.*—Entire; with the blade curled on one side, and the margin having a big curl in it.

*Disease and insect resistance.*—Highly resistant to nematode, and apparently immune to white fly (the two chief enemies of most Ligustrums), as determined from comparison with other Ligustrum varieties grown under comparable cultural conditions at Cairo, Georgia; has never required spraying.

FLOWER

Inflorescence: An erect, short, compact panicle from 2½ inches to 3 inches long and about 2 inches wide at the base, tapering to the tip; flowers sessile or sub-sessile on rachi of the branches.

Flower: Corolla tube slightly shorter than the limb, equalling the calyx; stamens exserted. Color—white.

Quantity of bloom: Abundant.

Fruit: Berry-like drupe; 1 to 4-seeded; usually only 1 or 2 fruits per inflorescence, if any develop. Color—black.

I claim:

A new and distinct variety of Ligustrum plant, substantially as herein shown and described, characterized particularly as to novelty by its dwarf and spreading habits of growth, by its short internodes, and by its abundant foliage which almost completely hides the woody stems between nodes.

No references cited.